United States Patent [19]
McGregor et al.

[11] Patent Number: 5,869,080
[45] Date of Patent: Feb. 9, 1999

[54] ABSORBABLE IMPLANT MATERIALS HAVING CONTROLLED POROSITY

[75] Inventors: James McGregor, Glasgow; Paul W. Watt, East Kilbride; Nicholas D. Light, Perthshire; Wilson Harvey, Stirling, all of United Kingdom

[73] Assignee: Johnson & Johnson Medical, Inc., Arlington, Tex.

[21] Appl. No.: 653,890

[22] Filed: May 28, 1996

[51] Int. Cl.⁶ ................................................. A61F 2/02
[52] U.S. Cl. ................................................. 424/426
[58] Field of Search .................. 424/422, 423, 424/426

[56] References Cited

U.S. PATENT DOCUMENTS

| | | |
|---|---|---|
| 4,606,910 | 8/1986 | Sawyer . |
| 5,326,350 | 7/1994 | Li .............................................. 623/11 |
| 5,466,462 | 11/1995 | Rosenthal et al. ...................... 424/426 |
| 5,565,210 | 10/1996 | Rosenthal et al. ...................... 424/426 |
| 5,571,181 | 11/1996 | Li .............................................. 623/11 |
| 5,610,148 | 3/1997 | Brown ...................................... 514/21 |

FOREIGN PATENT DOCUMENTS

| | | |
|---|---|---|
| 0 042 253 | 12/1981 | European Pat. Off. . |
| 0 314 109 | 5/1989 | European Pat. Off. . |
| 0 562 862 | 9/1993 | European Pat. Off. . |
| 0 562 864 | 9/1993 | European Pat. Off. . |
| 0 636 377 | 2/1995 | European Pat. Off. . |
| 0 645 149 | 3/1995 | European Pat. Off. . |
| 2 281 861 | 3/1995 | United Kingdom . |
| WO 95/05083 | 2/1995 | WIPO . |

*Primary Examiner*—Carlos A. Azpuru
*Attorney, Agent, or Firm*—Andrew C. Farmer

[57] ABSTRACT

Absorbable implant materials having controlled porosity are formed by a method comprising the steps of: providing a dispersion of a bioabsorbable polymer, such as collagen, in a first solvent, such as water; adding particles of a second material, e.g. frozen water droplets or ice particles to the dispersion; followed by freezing the dispersion to form a frozen dispersion having the particles embedded therein, and removing both the first solvent and the second material from the frozen dispersion by freeze-drying or solvent extraction to leave the porous implant material. The invention also encompasses the use of such implant materials for wound healing applications.

17 Claims, 4 Drawing Sheets

ABSORBABLE IMPLANT MATERIALS HAVING CONTROLLED POROSITY

FIELD OF THE INVENTION

The present invention relates to bioabsorbable materials having controlled porosity. The materials are especially suitable for use as implants or dressings in wound healing applications.

BACKGROUND OF THE INVENTION

A number of attempts have been made to fashion solid, bioabsorbable implant and/or dressing materials for application to wounds to protect the wounds and assist wound healing and tissue regeneration.

A solid wound implant material should preferably include the properties of gradual, controllable degradation and absorption in situ as the wound heals, low antigenicity, mechanical strength, conformability, and optimised porosity. The controlled porosity is important because the healing of wounds depends on the production by the wound of substantial quantities of matrix materials and granulation tissue involving the migration of fibroblast cells and connective tissue into the implant.

Various naturally occurring biopolymers, including proteins and polysaccharides, have been used over the last 20–30 years in the treatment of wounds or the augmentation of soft tissues. Proteins such as collagen, the most common animal protein and the main component of most connective tissues in the animal body, have been used due to their convenient physical properties and their high degree of bioacceptability. Collagen exists as many genetically distinct types, but the higher mammals share in common these types and the homology between the various types in, for example, man, cattle, sheep, pigs or chickens, is remarkably high. This means that the immunogenicity of animal collagens when implanted into humans, is very low and, therefore, that adverse reaction is very low. Furthermore, collagen and many other biopolymers actively assist wound healing by promoting the proliferation of fibroblasts, and by promoting angiogenesis.

Other proteins, especially those of the connective tissue matrix of man have been suggested as possible components of wound healing or tissue implant materials. These proteins include fibronectin, laminin and fibrin. Similarly, the high molecular weight polysaccharides of the connective tissue matrix have also been used in various types of wound dressing or "synthetic skins". These include such molecules as heparan sulphate, chondroitin sulphate, hyaluronic acid and dermatan sulphate. Other naturally occurring polysaccharide materials, especially of plant origin, have been cited as useful in the manufacture of dressings for wounds (e.g. alginates, guar gum, various plant gums) although not, in the main, in fabrication of implants as they are not bioabsorbable.

U.S. Pat. No. 4,970,298 (Frederick H. Silver et al) describes a biodegradable collagen matrix allegedly suitable for use as a wound implant. The matrix is formed by freeze drying an aqueous dispersion containing collagen, cross-linking the collagen via two cross-linking steps and freeze-drying the cross-linked matrix. The matrix may also contain hyaluronic acid and fibronectin.

EP-A-0274898 (Ethicon Inc.) describes an absorbable implant material having an open cell, foam-like structure and formed from resorbable polyesters, such as poly-p-dioxanone, other polyhydroxycarboxylic acids, polylactides or polyglycolides. The open-cell plastic matrix is reinforced with one or more reinforcing elements of a textile nature formed from a resorbable plastic and embedded in the matrix. The open-cell plastic matrix is made by freeze-drying a solution or suspension of the plastic material in a non-aqueous solvent. The pore size of the open-cell plastic matrix is from 10 to 200 $\mu$m.

JP-A-03023864 (Gunze KK) describes a wound implant material comprising a collagen sponge matrix reinforced with fibres of poly-L-lactic acid. The collagen sponge matrix is formed by freeze drying a solution of porcine atherocollagen.

EP-A-0562862 (Johnson & Johnson Medical, Inc.) describes bioabsorbable wound implant materials that are composites comprising a collagen sponge matrix having embedded therein oriented substructures of solid collagen fibers, films or flakes. The substructures reinforce the collagen sponge and also provide a scaffold for directional cellular migration into the implant. The composites are formed by immersing the substructures in an aqueous collagen slurry and then freeze-drying the slurry to form the collagen sponge matrix.

The above bioabsorbable sponge implants are formed by freeze-drying or solvent drying solutions or suspensions of a bioabsorbable material in a solvent. However, it is generally difficult to control the pore size and density of sponge materials made in this way. The structural integrity of these sponges has been enhanced by embedding bioabsorbable reinforcing fibres or substructures in the sponge matrix. The resorption of the sponges has been slowed by chemical cross-linking of the biopolymer.

Attempts have also been made to reduce the pore size of collagen sponges formed by freeze-drying. This was done in order both to increase the density of the sponges and to limit the pore size to the 50–250 $\mu$m range that was thought to be optimum for invasion by fibroblasts.

In particular, WO90/00060 (Collagen Corporation) describes collagen implants that are formed by flash freezing and then freeze-drying a suspension of collagen fibrils without chemical cross-linking. The flash freezing results in smaller ice crystals, and hence in smaller pores in the finished sponge. The implants have a bulk density of 0.01 to 0.3 g/cm$^3$ and a pore population in which at least about 80% of the pores have an average pore size of 35 to 250 $\mu$m. This wound healing matrix also serves as an effective sustained delivery system for bioactive agents.

Many of these sponge materials are intended for use in tissue augmentation or repair and require to be invaded and replaced by cells and newly synthesised connective tissue. In this regard, it is crucial that a material placed into a wound to replace lost tissue, or used to augment deficient tissue, should be rapidly colonised by cells and newly forming connective tissue. If this does not happen, the material will be rapidly exfoliated by the wound bed and granulation tissue which will form outside of the matrix.

It has now been found that larger pores, in the size range 0.1–3.0, preferably 0.3–1.0 mm, enhance fibroblast invasion rates and result in enhanced wound healing properties.

Wake et al in *Cell Transplantation* vol. 3(4), pp 339–343 (1994) describe studies of pore size effects on the fibrovascular tissue growth in porous bioabsorbable polymer substrates. The substrates of poly-L-lactic acid (PLLA) were prepared with pore sizes of up to 500 $\mu$m by a particulate leaching technique. Briefly, the PLLA was dissolved in methylene chloride and sieved sodium chloride particles having diameters similar to the desired pore size were dispersed in the solution. The resulting dispersion was then cast into disks and dried. The sodium chloride was then leached from the disks to leave the desired porous PLLA structure. It was found that fibrovascular tissue advances much faster into porous PLLA with a larger pore size (~500 μm) than into porous PLLA having smaller pores (179 and 91 μm).

Mikos et al in *Polymer* vol. 35(5), pages 1068–1077 (1994) describe the preparations of PLLA sponges by particulate leaching in more detail. They state that, when 70–90% by weight of sodium chloride particles is included in the PLLA, the resulting leached material is homogeneous with interconnected pores. There is no disclosure of leaching the sodium chloride from frozen aqueous dispersions of PLLA.

SUMMARY OF THE INVENTION

It is an object of the current invention to provide a new method of making sponge material suitable for use in wound healing therapy and the repair of tissues, for example, full and partial thickness defects of the skin, whereby said material has controlled and graded pores or spaces large and interconnected enough to encourage and support very rapid cellular invasion.

It is a further object of the invention to provide bioabsorbable sponge materials obtainable by the method of the invention and having controlled and graded pores or spaces as above.

It is a further object of the present invention to provide a new method of making sponge materials using aqueous suspensions of bioabsorbable materials.

It is a further object of the invention to provide the use of such an improved bioabsorbable sponge material made by a method according to the invention in the preparation of wound implants and/or wound dressings.

Accordingly, the present invention provides a method of making a bioabsorbable implant material having interconnected pores comprising the steps of: providing a dispersion of a bioabsorbable polymer in a first solvent; adding particles of a second material to the dispersion; followed by freezing the dispersion to form a frozen dispersion having the particles embedded therein, and removing said first solvent and second material from said frozen dispersion.

Removing both the first solvent and the second material from the frozen dispersion, for example by evaporation under vacuum (freeze drying), results in a solid bioabsorbable polymer comprising a sponge matrix having a structure somewhat similar to previously known bioabsorbable sponges, but also comprising therein larger interconnected pores corresponding in size and distribution to the dispersed particles in the frozen dispersion. Since the number and size of the particles in the frozen dispersion can readily be controlled, this method allows a sponge with high and controlled porosity to be made.

Preferably, the particles of the second material are frozen droplets or crushed and sieved frozen particles of a second solvent and the step of adding the frozen droplets or frozen particles to the dispersion is carried out while the dispersion is maintained at a temperature below the melting point of the second solvent. Where the second solvent is water and the dispersion is an aqueous dispersion, this may be achieved by adding up to 50% w/v of one or more low molecular weight alcohols such as ethanol or isopropanol to the dispersion in order to depress the freezing point of the dispersion. Preferably, 5 to 10% v/v of the low molecular weight alcohol is used.

In alternative preferred embodiments the first solvent comprises water and the second solvent comprises a water-immiscible oil or a volatile water-immiscible hydrocarbon such as hexane. In such cases, droplets of the liquid second solvent can be distributed in the dispersion of bioabsorbable polymer by standard mixing/emulsification processes. Emulsifiers may be added to stabilise the liquid droplets of the second solvent.

Preferably, the first solvent and second material are removed from the frozen dispersion by freeze drying. That is to say, the first solvent and second material are removed by evaporation under vacuum while heat is supplied to the frozen dispersion.

In alternative preferred embodiments of the method, the first solvent and second material are removed by solvent drying. In this method, the frozen dispersion is immersed in a liquid third solvent such as isopropanol maintained at a temperature above the freezing point of the dispersion. Repeated immersion in such a solvent bath, optionally with intermediate pressing steps, results in extraction of the solvent and second material from the frozen dispersion. Residual solvents remaining in the product can be removed by evaporation. This method is particularly suitable where the solvent is an aqueous solvent and the second material is a non-volatile liquid, such as an oil. Where the first solvent or second material comprises water, the third solvent is preferably a hygroscopic solvent such as anhydrous isopropanol. The technique of solvent drying has been described, for example, in U.S. Pat. No. 3,157,524.

Preferably, the bioabsorbable polymer comprises one or more biopolymers. More preferably, the bioabsorbable polymer consists essentially of the one or more biopolymers. Preferably, the biopolymers are selected from the group consisting of collagen, fibrin, laminin and fibronectin. More preferably, the bioabsorbable polymer consists essentially of collagen. The collagen may be of any origin or type, including fibrous insoluble collagen, atelocollagen, solubilised collagen or reprecipitated collagen.

In order to reduce the rate of dissolution and resorption of the implant material in situ, the method of the present invention preferably further comprises the step of treating the bioabsorbable polymer with a chemical cross-linking agent. More preferably, the bioabsorbable polymer comprises collagen and the cross-linking agent is HMDI (hexamethylene diisocyanate). Treatment with the cross-linking agent may be carried out on the dispersion of the bioabsorbable polymer either before or after addition of the droplets. Alternatively, cross-linking may be carried out on the finished implant material, e.g. by treatment with gaseous formaldehyde.

The principal advantage of the method of the present invention is that it allows the preparation of implant materials having high and controllable porosity. The finished materials contain interconnected pores corresponding substantially in size and distribution to the particles in the frozen dispersion. When preparing implant materials for wound healing applications, the particles preferably have diameters in the range 0.1 to 3.0 mm. More preferably, the particles have diameters in the range 0.3 to 1.0 mm. Preferably, the weight ratio of the particles to the dispersion of bioabsorbable polymer to which they are added is from 1:1 to 20:1. The resulting pores in the product material therefore occupy approximately 50% to 95% of the volume of the material.

The method of the present invention offers important advantages over the salt leaching method of preparing porous implants described by Wake et al and Mikos et al. In particular, in the method of the present invention the removal of the first solvent and of the second material is carried out in a single process step, thereby reducing process cost and complexity. In addition the present invention allows the production of aqueous based implant materials, such as proteins and polysaccharides. Furthermore, the particles of the second material can be made in a variety of shapes, including chips, rods, and beads. The incorporation of rods or chips will result in a structure containing many interconnecting channels, which would allow rapid cell invasion. Furthermore, the present invention enables the implant materials to be cast in any desired shape, whereas the salt leaching process previously described is effectively limited to thin films. Another advantage of the method of the present invention is that improved control over the density and porosity of the resulting materials can be achieved because the amount and composition of the first solvent in the frozen dispersion provide additional control parameters.

The present invention also provides a porous bioabsorbable implant material obtainable by a process according to the invention.

The present invention further provides the use of a porous bioabsorbable material obtainable by a process according to the invention for the preparation of an implant or dressing for the treatment of wounds.

BRIEF DESCRIPTION OF THE DRAWINGS

Specific embodiments of the present invention will now be described further, by way of example, with reference to the accompanying figures, in which.

DETAILED DESCRIPTION

EXAMPLE 1 (COMPARATIVE)

Fibrous collagen was obtained from bovine hides in pure form as an insoluble slurry in water, as described in U.S. Pat. No. 4,320,201 and U. Pat. No. 3,823,212, the entire contents of which are hereby expressly incorporated by reference. The fibrous slurry is made basic with sodium hydroxide to pH 9.0, and water is added to adjust the solids concentration to 5% by weight.

The aqueous dispersion of collagen fibers is then diluted to 0.5% solids. A cross-linker, HMDI (hexamethylene diisocyanate), is added in an amount corresponding to 5%by weight of the collagen in the dispersion with mixing, and the mixture is then snap frozen in a blast freezer. The frozen dispersion is then dried by freeze drying under standard conditions.

Figure 1:
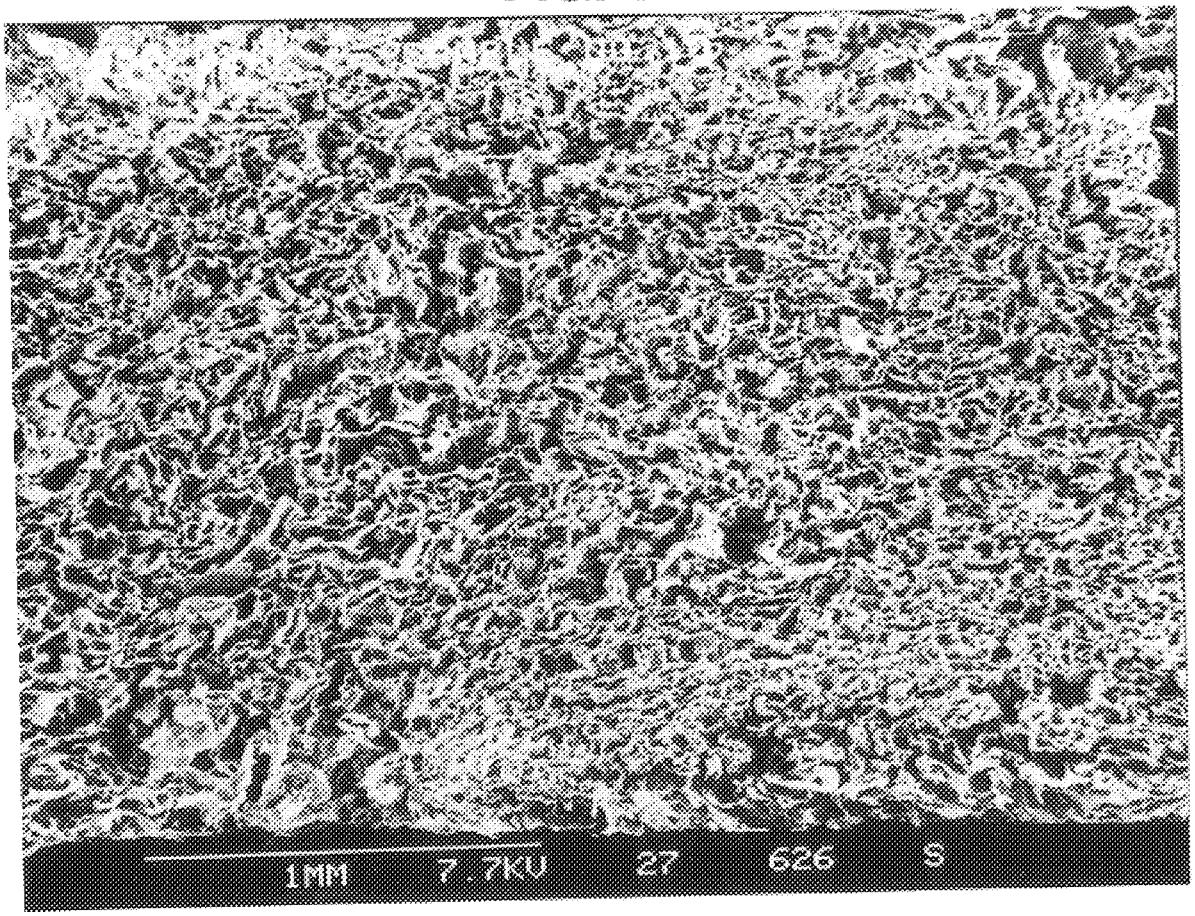
FIG. 1 shows a scanning electron micrograph of a collagen sponge implant material obtained by a prior art method.

A cross-section through a collagen sponge made in this way is shown in FIG. 1. It can be seen that the sponge comprises interconnected pores. The median pore size is approximately 0.1 mm.

EXAMPLE 2

An aqueous dispersion of collagen fibers is prepared as described above in Example 1. Absolute ethanol and water are then added to the dispersion to a final concentration of 10% v/v ethanol and 5% w/v solids. The dispersion is then cooled to $-6°$ C.

Ice particles are prepared by impacting ice contained in a plastic bag with a hammer and then sieving through a 2 mm sieve while maintaining the temperature below $-10°$ C. The sieved ice particles are then added to the pre-cooled collagen dispersion at a weight ratio of 9 parts ice particles to 1 part dispersion, such that the final collagen solids concentration in the mixture is 0.5% by weight. HMDI is added in an amount corresponding to 5% by weight of the collagen in the dispersion with mixing, and the mixture is then snap frozen in a blast freezer. The frozen dispersion is then dried by freeze drying under standard conditions.

Figure 2:
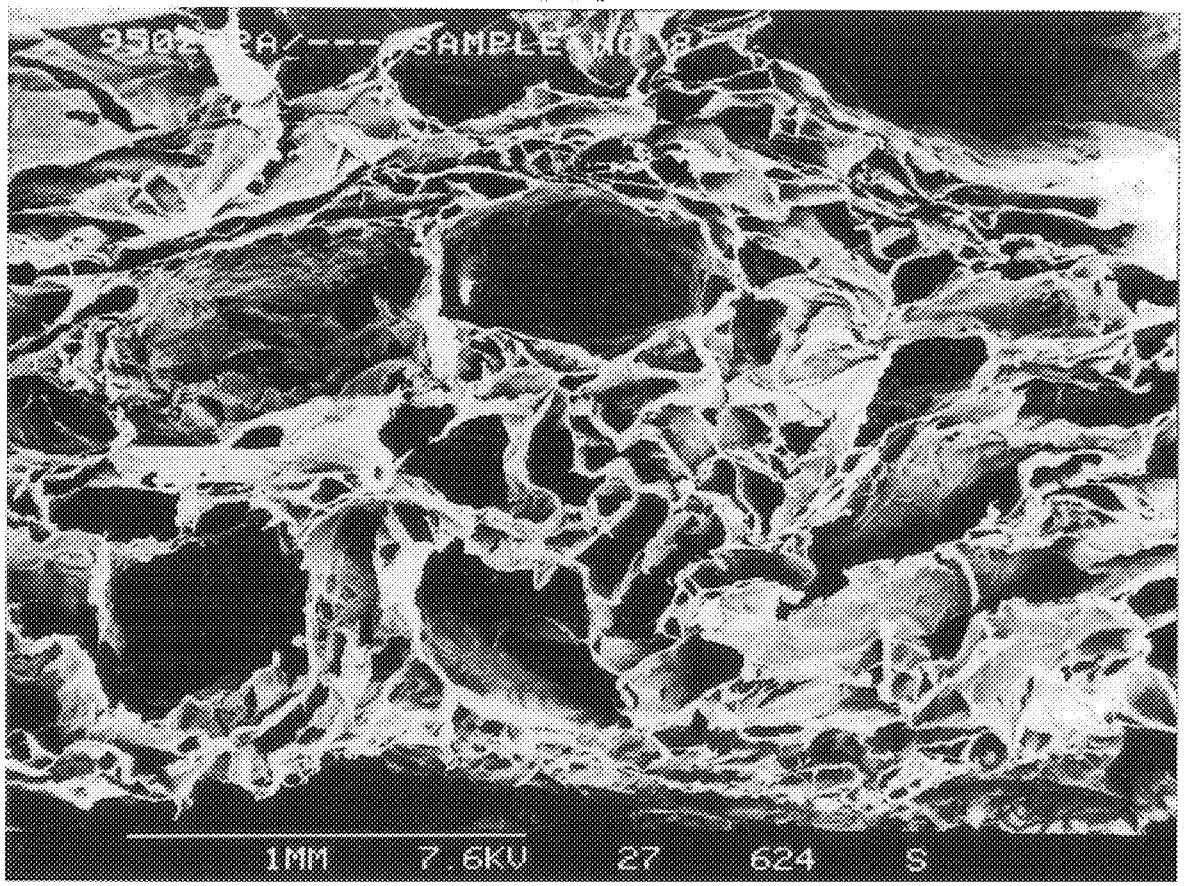
FIG. 2 shows a scanning electron micrograph, on the same scale as FIG. 1, of a collagen sponge implant obtained by a process according to the present invention.

A cross-section through a collagen sponge made as described in this Example is shown in FIG. 2. It can be seen that the sponge comprises interconnected pores. A number of these pores are quite large. The large pores are the vacancies left behind by evaporation of the ice particles from the frozen collagen dispersion. Typical dimensions for these large pores are 0.3–1.0 mm.

EXAMPLE 3

An aqueous dispersion of collagen fibers is prepared as described above in Example 1. Absolute ethanol and water are then added to the dispersion to a final concentration of 10% v/v ethanol and 5% w/w solids. The dispersion is then cooled to $-5°$ C.

Frozen water droplets of graded size 0.3 to 1.0 mm are made by firing a stream of physically well separated water droplets into a freezing solution such as isopropyl alcohol at $-20$ degrees C., or liquid nitrogen. The droplets are collected and stored at $-15°$ C.

The frozen water droplets are added to the pre-cooled dispersion of collagen fibers at a weight ratio of 9 parts water droplets to 1 part dispersion, such that the final collagen solids concentration in the mixture is 0.5% by weight. HMDI is added in an amount corresponding to 5% by weight of the collagen in the dispersion with mixing, and the mixture is then snap frozen in a blast freezer. The frozen dispersion is then dried by freeze drying under standard conditions.

EXAMPLE 4

An aqueous dispersion of collagen fibers is prepared as described above in Example 1. Liquid vegetable oil is added to the cold dispersion maintained at $1°$ C. in amounts ranging from 5%–100% by weight of the collagen present. In two different experiments, the oil is added in the presence and absence of 0.5% by weight of soluble collagen as an emulsifying agent. HMDI is added as a cross-linking agent in an amount of 5% by weight of the collagen, and the mixture is immediately vigorously mixed in an emulsifying homogeniser until a dispersion of oil droplets of diameter 0.1 to 0.5 mm is obtained. At this point the mixture is snap frozen in a blast freezer. The product is then thawed slowly in a bath of isopropanol with constant, gentle agitation until all of the oil is extracted (as assessed by grinding the product and extracting with standard fat extraction methods). It is necessary to change the isopropanol for fresh solvent in cases where high concentrations of oil are used. The products are then either air dried or washed in water and freeze dried.

EXAMPLE 5

An aqueous dispersion of collagen fibers is prepared as described above in Example 1.

Solid droplets of palm oil (solid at room temperature) are made by dropping palm oil liquid at 45° C. into a pre-cooled water bath at 1° C. The droplets are harvested and mixed with the collagen dispersion in the absence of alcohol in the same way as described in Example 1. Extraction of the palm oil and drying are performed as described in Example 2 above.

EXAMPLE 6

The enhanced cellular infiltration properties of the wound implant materials made according to the present invention are now demonstrated as follows.

Collagen sponge materials made in the fashion described above in Examples 1 and 2 are implanted subcutaneously in rats. The sponges are removed after one, three, seven and fourteen days. Portions of each sponge are taken for histological analysis.

Figure 3:
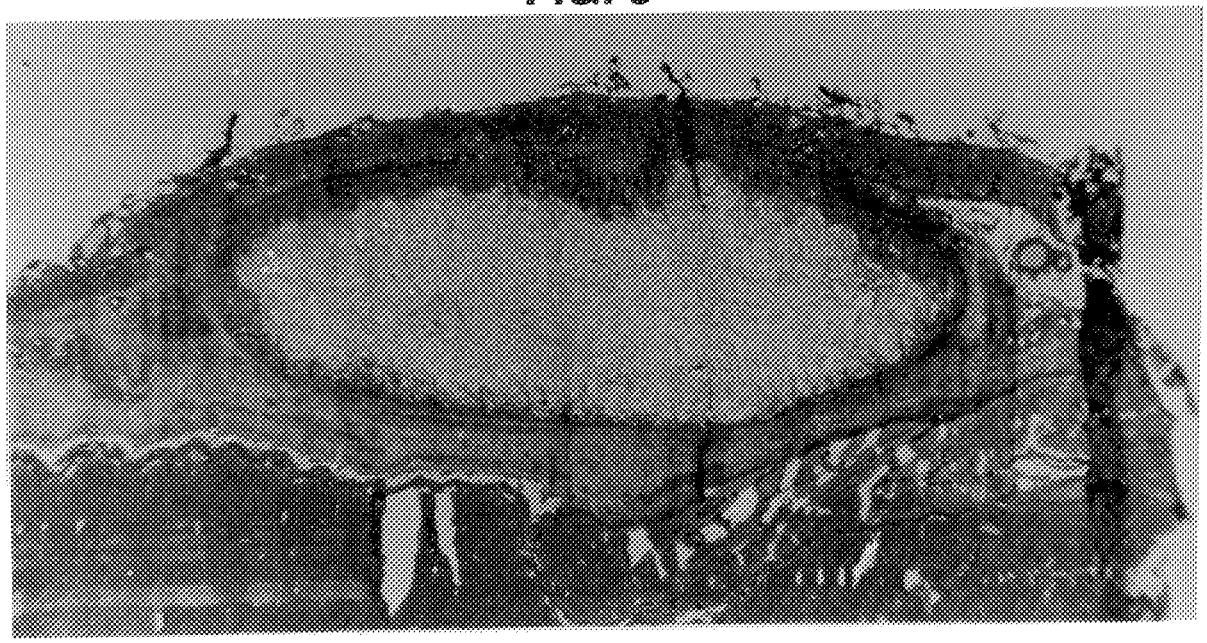
FIG. 3 shows a section through a prior art sponge similar to that of FIG. 1 taken 14 days after implantation in vivo.
Figure 4:
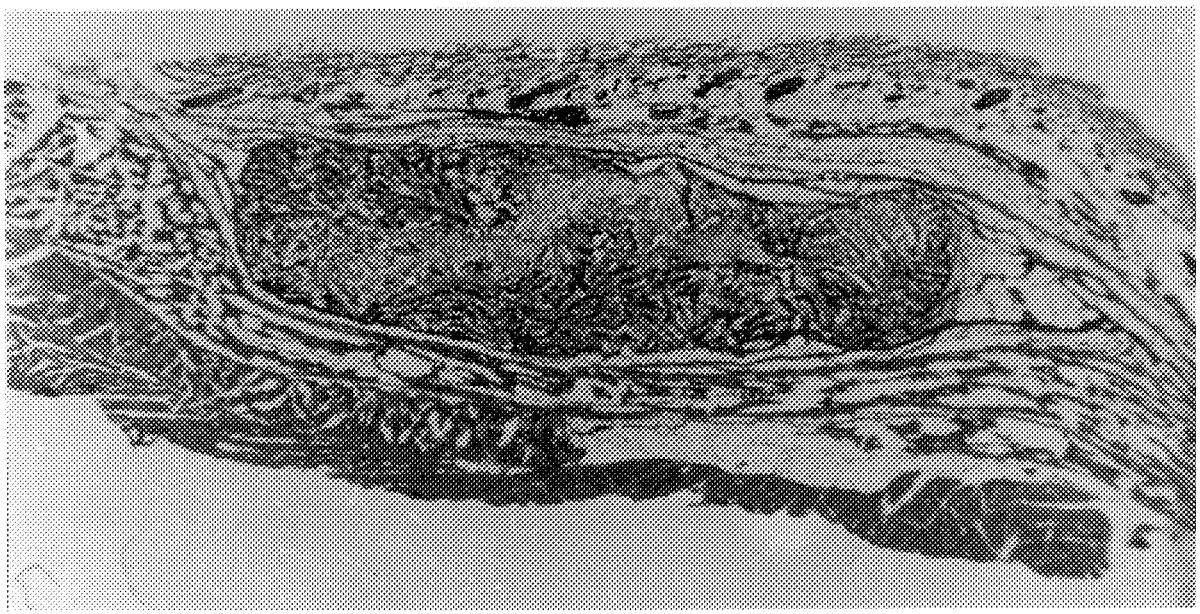
FIG. 4 shows a section through a sponge according to the present invention similar to that of FIG. 3, also sectioned 14 days after implantation in vivo.

FIGS. 3 and 4 illustrate the different rates of cellular invasion into prior art sponges (FIG. 3) and the sponge made according to the present invention (FIG. 4). It can clearly be seen that, after 14 days, there has been quite little cellular invasion into the sponge of FIG. 3, but substantial cellular invasion into the sponge of FIG. 4. This conclusion is confirmed by histological analysis of the implanted sponges.

The above embodiments have been described by way of example only. Many other embodiments of the invention falling within the scope of the accompanying claims will be apparent to the skilled reader.

We claim:

1. A method of making a bioabsorbable material having interconnecting pores comprising the steps of:
   providing a dispersion of a bioabsorbable polymer in a first solvent capable of dissolving or suspending said bioabsorbable polymer;
   adding particles of a second material, which is capable of being removed from said dispersion by freeze drying or solvent drying, to the dispersion; followed by freezing the dispersion to form a frozen dispersion having the particles embedded therein, and
   removing said first solvent and the particles of the second material from said frozen dispersion in a single step by freeze drying or solvent drying, the removal of the particles thereby forming the pores.

2. A method according to claim 1, wherein the particles of the second material are frozen droplets or frozen particles of a second solvent, which is capable of being frozen, and said adding step is carried out while the dispersion is maintained at a temperature below the melting point of the second solvent.

3. A method according to claim 2, wherein the first and second solvents comprise the same liquid.

4. A method according to claim 1, wherein the said particles are droplets of a second solvent which is immiscible in the first solvent.

5. A method according to claim 1, wherein the step of removing comprises removing the first solvent and second material by freeze drying.

6. A method according to claim 1, wherein the steps of removing comprises removing the first solvent and the second material by solvent drying.

7. A method according to claim 1, wherein the first solvent comprises water.

8. A method according to claim 1, wherein the bioabsorbable polymer comprises one or more biopolymers.

9. A method according to claim 8, wherein the biopolymers are selected from the group consisting of collagen, fibrin, laminin and fibronectin.

10. A method according to claim 8, wherein the bioabsorbable polymer consists essentially of collagen.

11. A method according to claim 1, further comprising the step of treating the bioabsorbable polymer with a chemical cross-linking agent.

12. A method according to claim 1 wherein at least some of said particles have a minimum dimension in the range 0.1–3.0 mm.

13. A method according to claim 12, wherein at least some of said particles have a minimum dimension in the range 0.3–1.0 mm.

14. A method according to claim 1, wherein the weight ratio of said particles to said dispersion of bioabsorbable polymer is from 1:1 to 20:1.

15. A porous bioabsorbable implant material obtainable by a process according to claim 1.

16. An implant or dressing for the treatment of wounds comprising a porous bioabsorbable material according to claim 15.

17. A method of treating a wound comprising applying thereto or thereinto a porous bioabsorbable material according to claim 15.

* * * * *

UNITED STATES PATENT AND TRADEMARK OFFICE
CERTIFICATE OF CORRECTION

PATENT NO.    : 5,869,080
DATED         : February 9, 1999
INVENTOR(S)   : James McGregor, Paul W. Watt, Nicholas D. Light and Wilson Harvey It is certified that error appears in the above-identified patent and that said Letters Patent is hereby corrected as shown below:

Column 8,
Line 14, please delete the word "steps" and insert -- step --

Signed and Sealed this

Twenty-eighth Day of May, 2002

Attest:

*Attesting Officer*

JAMES E. ROGAN
*Director of the United States Patent and Trademark Office*